United States Patent

Tsujita

(10) Patent No.: US 8,988,462 B2
(45) Date of Patent: Mar. 24, 2015

(54) ULTRASONIC DIAGNOSTIC APPARATUS AND ULTRASONIC IMAGE DISPLAY METHOD

(75) Inventor: Takehiro Tsujita, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 366 days.

(21) Appl. No.: 13/521,113

(22) PCT Filed: Feb. 3, 2011

(86) PCT No.: PCT/JP2011/052220
§ 371 (c)(1),
(2), (4) Date: Jul. 9, 2012

(87) PCT Pub. No.: WO2011/099410
PCT Pub. Date: Aug. 18, 2011

(65) Prior Publication Data
US 2012/0287156 A1 Nov. 15, 2012

(30) Foreign Application Priority Data
Feb. 9, 2010 (JP) ................................. 2010-026428

(51) Int. Cl.
| | |
|---|---|
| G09G 5/00 | (2006.01) |
| A61B 8/08 | (2006.01) |
| A61B 8/06 | (2006.01) |
| A61B 8/13 | (2006.01) |
| A61B 8/14 | (2006.01) |
| A61B 8/00 | (2006.01) |

(52) U.S. Cl.
CPC . *A61B 8/523* (2013.01); *A61B 8/06* (2013.01); *A61B 8/13* (2013.01); *A61B 8/14* (2013.01); *A61B 8/461* (2013.01); *A61B 8/485* (2013.01)
USPC ........................................................ 345/629

(58) Field of Classification Search
None
See application file for complete search history.

(56) References Cited

U.S. PATENT DOCUMENTS

| | | | |
|---|---|---|---|
| 2007/0293755 A1 | 12/2007 | Shirahata et al. | |
| 2008/0260227 A1* | 10/2008 | Hayashi et al. | ................ 382/131 |
| 2010/0022878 A1* | 1/2010 | Azuma et al. | ................. 600/443 |

FOREIGN PATENT DOCUMENTS

| | | |
|---|---|---|
| JP | A-2006-130071 | 5/2006 |
| JP | A-2008-259605 | 10/2008 |
| JP | A-2008-284287 | 11/2008 |
| WO | WO 2006/030731 A1 | 3/2006 |
| WO | WO 2006/033377 A1 | 3/2006 |

OTHER PUBLICATIONS

International Search Report issued in International Patent Application No. PCT/JP2011/052220 dated Apr. 12, 2011.

* cited by examiner

*Primary Examiner* — Ryan R Yang
(74) *Attorney, Agent, or Firm* — Oliff PLC

(57) ABSTRACT

In order to provide an ultrasonic diagnostic apparatus and an ultrasonic image display method for appropriately displaying a three-dimensional elastic image, a three-dimensional blood flow image, and a three-dimensional tomographic image such that the images can be separately recognized, the ultrasonic diagnostic apparatus includes projected image creation units that create a plurality of projected images from the plurality of types of volume data and a projected image combination unit that creates a composite projected image by combining the plurality of projected images on the basis of a predetermined combination rate, and the display unit displays the composite projected image.

13 Claims, 6 Drawing Sheets

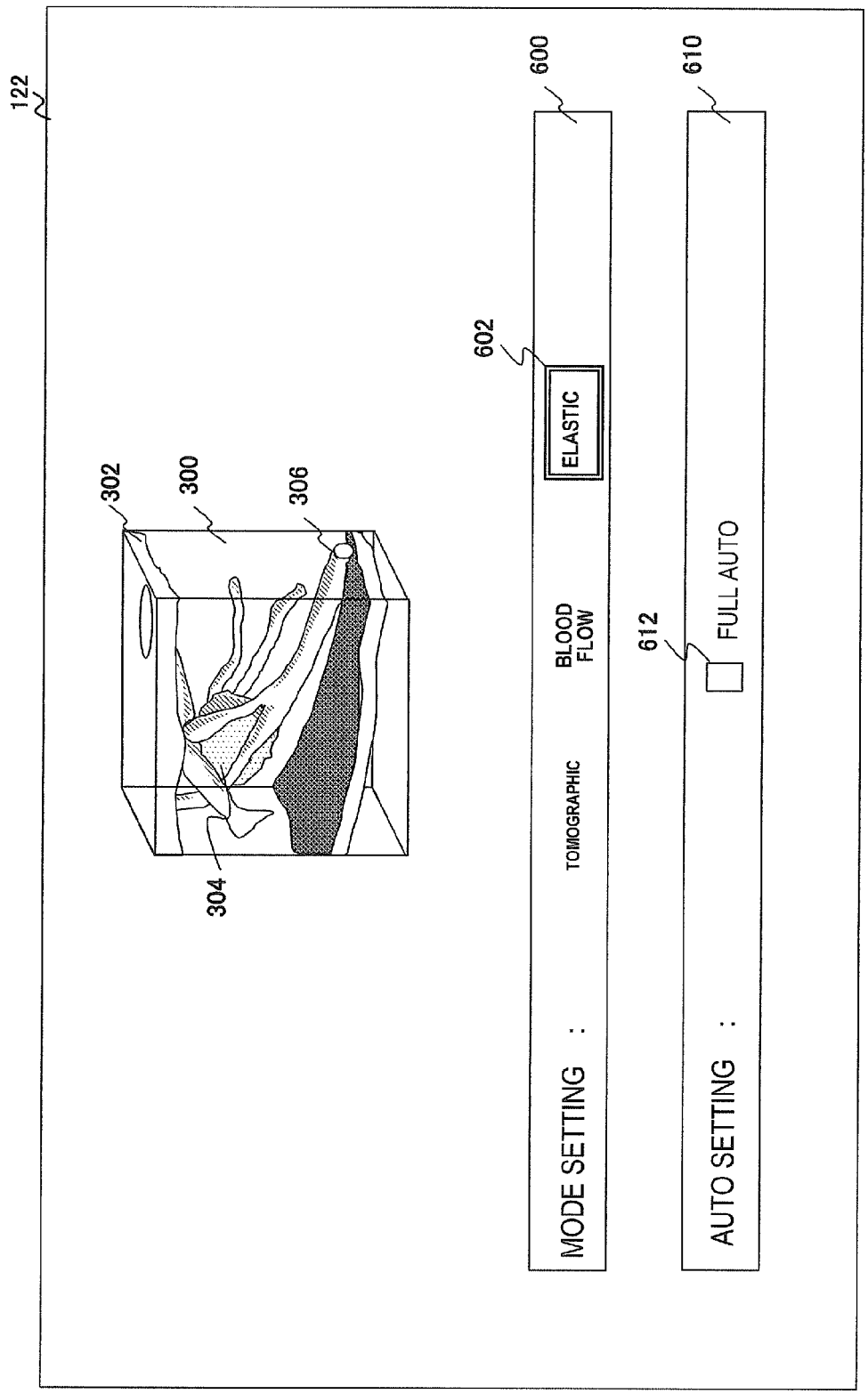

ULTRASONIC DIAGNOSTIC APPARATUS AND ULTRASONIC IMAGE DISPLAY METHOD

TECHNICAL FIELD

The present invention relates to an ultrasonic diagnostic apparatus and an ultrasonic image display method for displaying a three-dimensional elastic image, which shows the hardness or softness of body tissue of an object, using ultrasonic waves.

BACKGROUND ART

The ultrasonic diagnostic apparatus can transmit an ultrasonic wave into the object using an ultrasonic probe to obtain and display a three-dimensional tomographic image and a three-dimensional elastic image on the basis of a received signal which is received from the body tissue inside the object.

When displaying a three-dimensional elastic image on a three-dimensional tomographic image so as to overlap each other, the opacity of the three-dimensional tomographic image is set so that the shape or the volume of a hard portion or a soft portion of the three-dimensional elastic image can be recognized (for example, PTL 1).

CITATION LIST

Patent Literature

[PTL 1] JP-A-2008-259605

SUMMARY OF INVENTION

Technical Problem

Although PTL 1 discloses a method of setting the opacity of a three-dimensional tomographic image, a method of displaying a three-dimensional elastic image, a three-dimensional blood flow image, and a three-dimensional tomographic image simultaneously is not disclosed. For this reason, elastic information in the three-dimensional elastic image and blood flow information in the three-dimensional blood flow image may be mixed. As a result, there has been a possibility that a region of interest (for example, a hard region (tumor) in the three-dimensional elastic image) which it is desirable to observe will be hidden by another image.

It is an object of the present invention to display a three-dimensional elastic image, a three-dimensional blood flow image, and a three-dimensional tomographic image such that the images can be recognized separately.

Solution to Problem

In order to achieve the object of the present invention, an ultrasonic diagnostic apparatus includes: an ultrasonic probe having transducers through which an ultrasonic wave is transmitted and received; a signal transmission unit that transmits an ultrasonic wave to an object through the ultrasonic probe; a signal receiving unit that receives a reflected echo signal reflected from the object; a display unit that creates a projected image by rendering a plurality of types of volume data based on the reflected echo signal and displays the projected image; a projected image creation unit that creates a plurality of projected images from the plurality of types of volume data; and a projected image combination unit that creates a composite projected image by combining the plurality of projected images on the basis of a predetermined combination rate. The display unit displays the composite projected image. Accordingly, it is possible to display a three-dimensional elastic image, a three-dimensional blood flow image, and a three-dimensional tomographic image such that each of the images can be recognized as a composite projected image.

Specifically, a first projected image creation unit, which creates a first projected image using volume data selected from the plurality of types of volume data, and a second projected image creation unit, which creates a second projected image different from the first projected image using volume data selected from the plurality of types of volume data, are provided. The projected image combination unit creates the composite projected image by combining the first and second projected images on the basis of a predetermined combination rate of the first and second projected images.

Advantageous Effects of Invention

According to the present invention, it is possible to display a three-dimensional elastic image, a three-dimensional blood flow image, and a three-dimensional tomographic image such that the images can be separately recognized.

BRIEF DESCRIPTION OF DRAWINGS

FIG. 6 is a view showing a display form of a display unit 122 in the second and third embodiments of the present invention.

DESCRIPTION OF EMBODIMENTS

An ultrasonic diagnostic apparatus 100 to which the present invention is applied will be described using FIG. 1.

Figure 1:
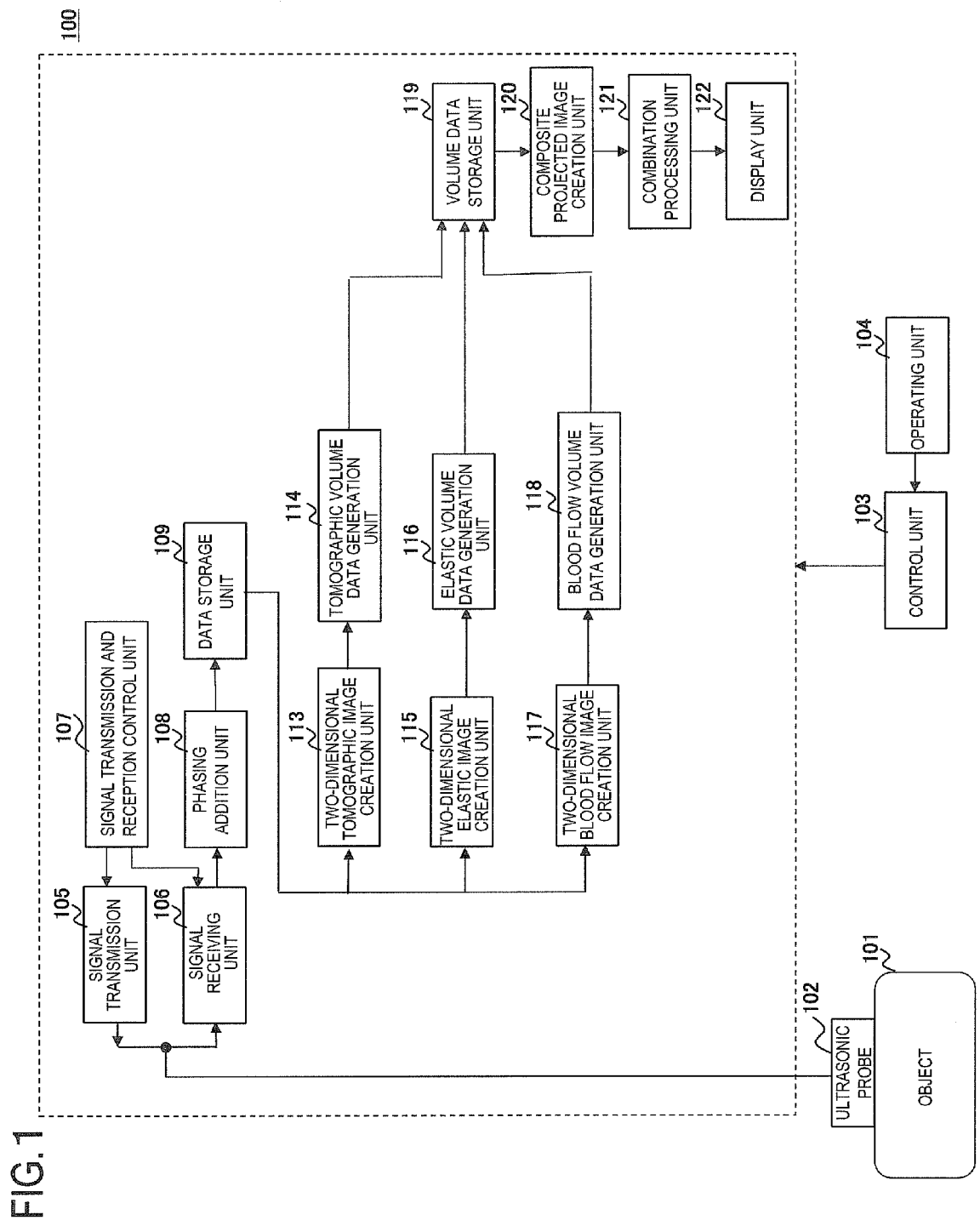
FIG. 1 is a view showing a block diagram of the general configuration of the present invention.

As shown in FIG. 1, the ultrasonic diagnostic apparatus 100 includes: an ultrasonic probe 102 used by making contact with an object 101; a signal transmission unit 105 that repeatedly transmits an ultrasonic wave to the object 101 through the ultrasonic probe 102 at fixed intervals; a signal receiving unit 106 that receives a reflected echo signal reflected from the object 101; a signal transmission and reception control unit 107 that controls the signal transmission unit 105 and the signal receiving unit 106; and a phasing addition unit 108 that performs phasing addition of the reflected echo received by the signal receiving unit 106.

The ultrasonic probe 102 is formed by arraying a plurality of transducers, and has a function of transmitting and receiving an ultrasonic wave to and from the object 101 through the transducers. The ultrasonic probe 102 is formed by arraying a plurality of rectangular or fan-shaped transducers, and can transmit and receive an ultrasonic wave in a three-dimensional manner by mechanically vibrating the transducers in a direction perpendicular to the arrangement direction of the plurality of transducers. In addition, it is also possible to use the ultrasonic probe 102 in which a plurality of transducers are arrayed in a two-dimensional manner so that transmission and reception of ultrasonic waves can be electronically controlled.

The signal transmission unit 105 drives the transducers of the ultrasonic probe 102 to generate a carrier pulse for generating an ultrasonic wave. The signal transmission unit 105 has a function of setting the convergent point of transmitted ultrasonic waves at a certain depth. In addition, the signal receiving unit 106 generates an RF signal, that is, a received signal by amplifying the reflected echo signal received by the ultrasonic probe 102 with a predetermined gain. The signal transmission and reception control unit 107 is for controlling the signal transmission unit 105 or the signal receiving unit 106.

The phasing addition unit 108 controls the phase of the RF signal amplified by the signal receiving unit 106, and generates RF signal frame data (equivalent to RAW data) by forming ultrasonic beams at one or a plurality of convergent points.

In addition, the ultrasonic diagnostic apparatus 100 includes: a data storage unit 109 that stores RF signal frame data generated by the phasing addition unit 108; a two-dimensional tomographic image creation unit 113 that creates a two-dimensional tomographic image on the basis of the RF signal frame data stored in the data storage unit 109; a tomographic volume data generation unit 114 that generates tomographic volume data by performing three-dimensional coordinate transformation of the two-dimensional tomographic image created by the two-dimensional tomographic image creation unit 113 on the basis of the acquisition position of the two-dimensional tomographic image; a two-dimensional elastic image creation unit 115 that creates a two-dimensional elastic image on the basis of a plurality of RF signal frame data items stored in the data storage unit 109; an elastic volume data generation unit 116 that generates elastic volume data by performing three-dimensional coordinate transformation of the two-dimensional elastic image created by the two-dimensional elastic image creation unit 115 on the basis of the acquisition position of the two-dimensional elastic image; a two-dimensional blood flow image creation unit 117 that creates a two-dimensional blood flow image by calculating blood flow information, such as the speed of blood flow or the amount of blood flow (power), on the basis of the plurality of RF signal frame data items stored in the data storage unit 109; a blood flow volume data generation unit 118 that generates blood flow volume data by performing three-dimensional coordinate transformation of the two-dimensional blood flow image created by the two-dimensional blood flow image creation unit 117 on the basis of the acquisition position of the two-dimensional blood flow image; a volume data storage unit 119 that stores the tomographic volume data, the elastic volume data, and the blood flow volume data which have been generated; a composite projected image creation unit 120 that sequentially reads the respective volume data items stored in the volume data storage unit 119 and creates a composite projected image; a combination processing unit 121 that performs various kinds of processing on the composite projected image; and a display unit 122 that displays the composite projected image, the two-dimensional tomographic image, and the like.

In addition, the ultrasonic diagnostic apparatus 100 includes a control unit 103 that controls each of the components described above and an operating unit 104 for performing various inputs to the control unit 103. The operating unit 104 includes a keyboard, a track ball, and the like.

The two-dimensional tomographic image creation unit 113 creates a two-dimensional tomographic image by performing signal processing, such as gain correction, log compression, detection, edge enhancement, and filtering, on the input RF signal frame data output from the data storage unit 109 on the basis of the setting conditions in the control unit 103.

The ultrasonic probe 102 can measure the signal transmission and reception direction (θ, φ) simultaneously with transmission and reception of ultrasonic waves, and the tomographic volume data generation unit 114 generates tomographic volume data by performing three-dimensional transformation of a plurality of two-dimensional tomographic images on the basis of the signal transmission and reception direction (θ, φ) equivalent to the acquisition position of the two-dimensional tomographic images. A tomographic code is given to each point of tomographic volume data according to the signal strength of a received signal. The tomographic code is a code (for example, 256 gray-scale levels (8 bits)) for assigning the RGB values.

The two-dimensional elastic image creation unit 115 measures displacement from a plurality of RF signal frame data items stored in the data storage unit 109. Then, the two-dimensional elastic image creation unit 115 creates a two-dimensional elastic image by calculating the value of elasticity on the basis of the measured displacement. For example, the value of elasticity is any of the elastic information including the strain, elastic modulus, displacement, viscosity, distortion ratio, and the like.

The elastic volume data generation unit 116 generates elastic volume data by performing three-dimensional transformation of a plurality of two-dimensional elastic images on the basis of the signal transmission and reception direction (θ, φ) equivalent to the acquisition position of the two-dimensional elastic images. An elastic code is given to each point of elastic volume data according to the value of elasticity. The elastic code is a code (for example, 256 gray-scale levels (8 bits)) for assigning the RGB values.

The two-dimensional blood flow image creation unit 117 calculates blood flow information, such as the speed of blood flow or the amount of blood flow (power), from the plurality of RF signal frame data items stored in the data storage unit 109 using the Doppler frequency shift. In addition, the two-dimensional blood flow image creation unit 117 creates a two-dimensional blood flow image on the basis of the calculated blood flow information.

The blood flow volume data generation unit 118 generates blood flow volume data by performing three-dimensional transformation of a plurality of two-dimensional blood flow images on the basis of the signal transmission and reception direction (θ, φ) equivalent to the acquisition position of the two-dimensional blood flow images. A blood flow code is given to blood flow volume data according to the blood flow information (blood flow speed, blood flow direction, and dispersion). The blood flow code is a code (for example, 256 gray-scale levels (8 bits)) for assigning the RGB values.

As a plurality of types of volume data, the volume data storage unit 119 stores the tomographic volume data generated by the tomographic volume data generation unit 114, the elastic volume data generated by the elastic volume data generation unit 116, and the blood flow volume data generated by the blood flow volume data generation unit 118.

The composite projected image creation unit 120 creates a plurality of projected images by reading the plurality of types of volume data stored in the volume data storage unit 119 and creates a composite projected image by combining the plurality of created projected images. The projected image is a three-dimensional image created by rendering of volume data onto the two-dimensional projection plane.

Figure 2:
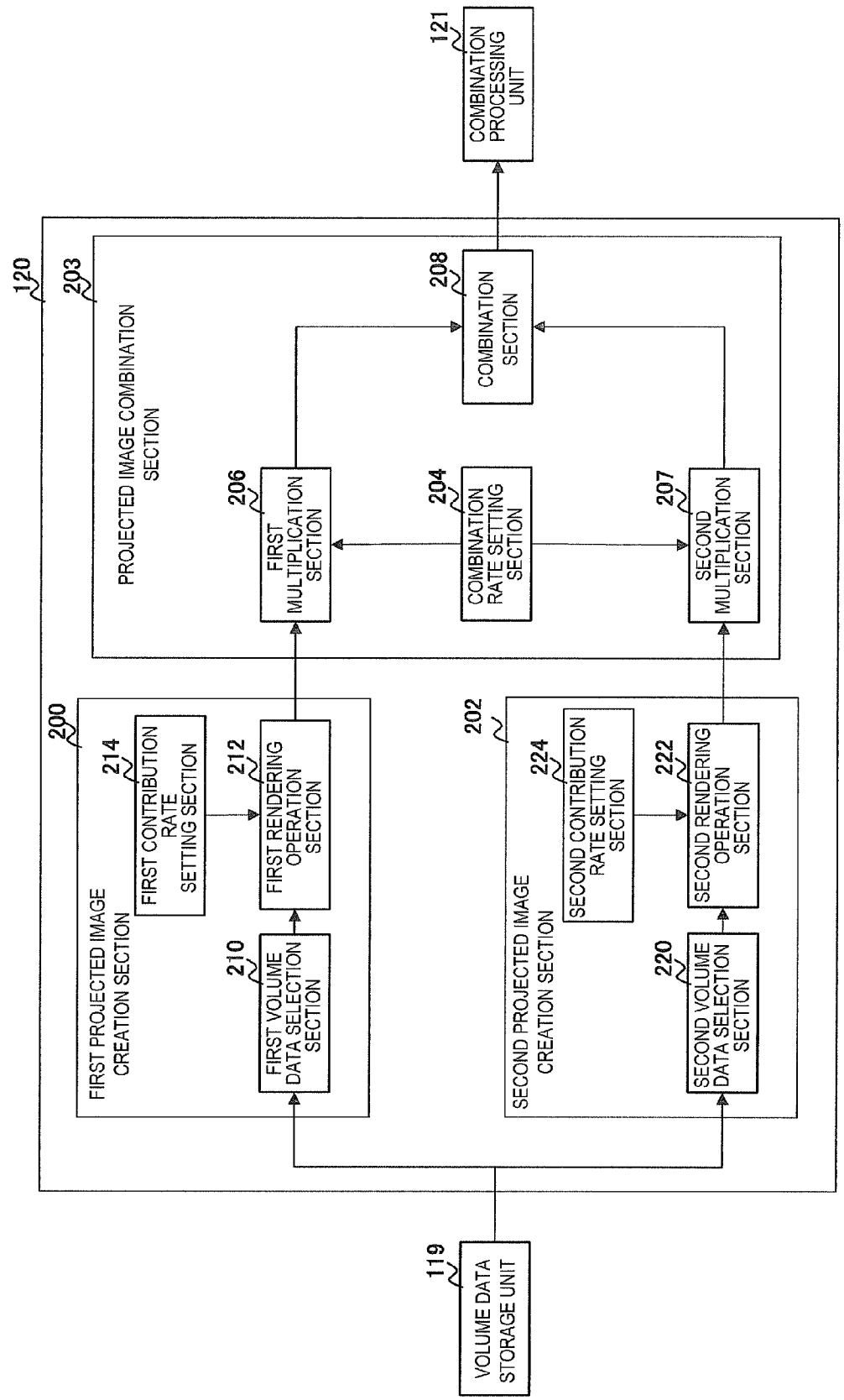
FIG. 2 is a view showing the details of a composite projected image creation unit 120 in a first embodiment of the present invention.
Figure 3:
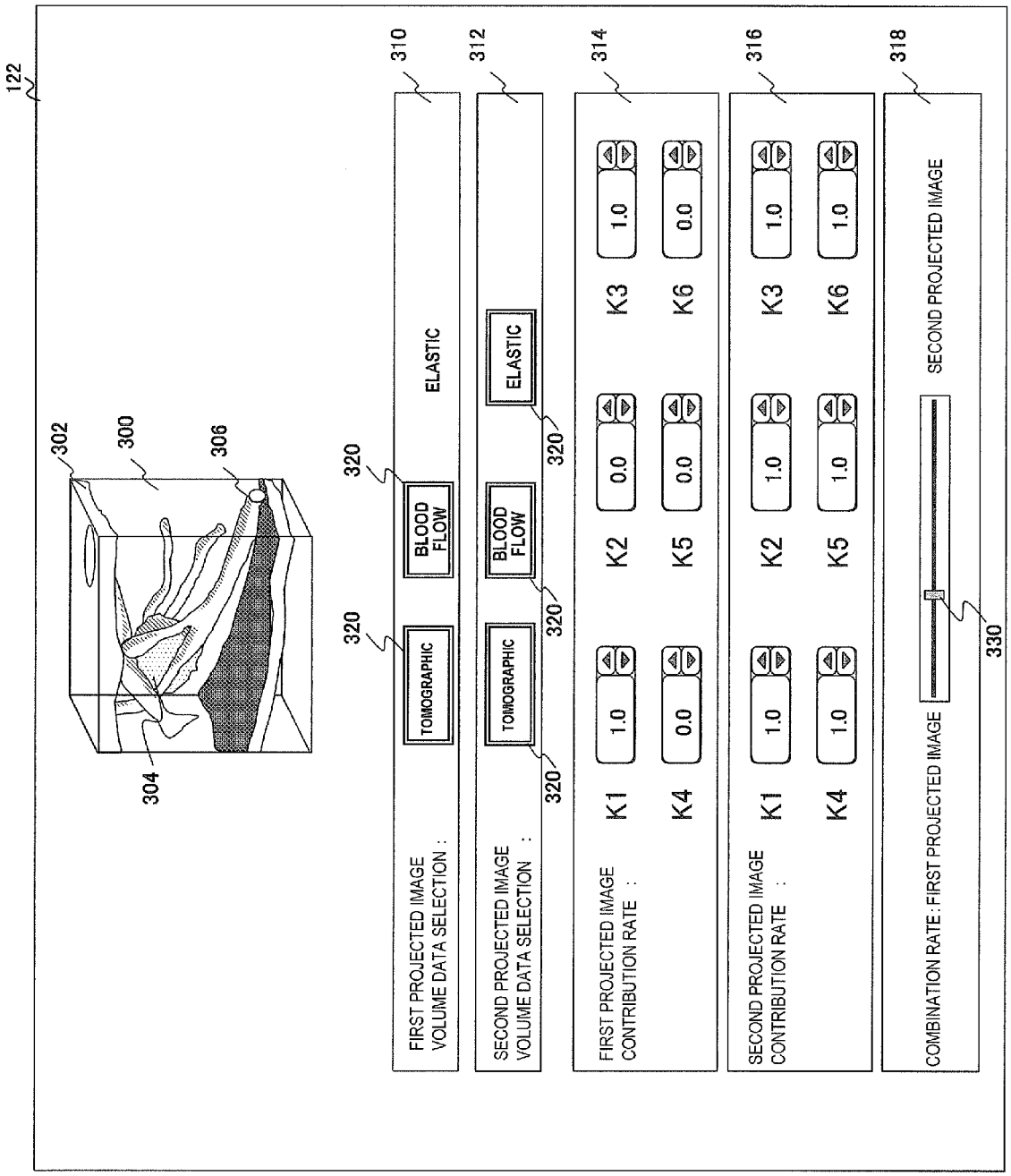
FIG. 3 is a view showing a display form of a display unit 122 in the first embodiment of the present invention.

The composite projected image creation unit 120 will be described using FIGS. 2 and 3. FIG. 2 shows details of the composite projected image creation unit 120, and FIG. 3 shows a settings screen (graphic user interface) of various parameters of the composite projected image creation unit 120 displayed on the display unit 122. Graphics, such as numeric values and bars, are used for the settings screen for various parameters, so that various parameters can be set under the control of the control unit 103 based on the operation of the operating unit 104.

The composite projected image creation unit 120 includes projected image creation sections 200 and 202, which create a plurality of projected images from the plurality of types of volume data, and a projected image combination section 203, which creates a composite projected image by combining the plurality of projected images on the basis of a predetermined combination rate for combining the plurality of projected images.

Specifically, the composite projected image creation unit 120 includes: the first projected image creation section 200 which creates a first projected image using the predetermined volume data selected from a plurality of types of volume data by the operator; the second projected image creation section 202 which creates a second projected image, which is different from the first projected image, using the predetermined volume data selected from a plurality of types of volume data by the operator; and a projected image combination section 203 which creates a composite projected image by combining the first and second projected images on the basis of the predetermined combination rate of the first and second projected images.

The first projected image creation section 200 includes; a first volume selection section 210 which selects predetermined volume data from the plurality of types of volume data stored in the volume data storage unit 119; a first contribution rate setting section 214 which sets the contribution rate of other volume data in volume rendering of the volume data selected by the first volume selection section 210; and a first rendering operation section 212 which creates a first projected image by performing volume rendering of the selected volume data on the basis of the set contribution rate.

The second projected image creation section 202 includes: a second volume selection section 220 which selects predetermined volume data from the plurality of types of volume data stored in the volume data storage unit 119; a second contribution rate setting section 224 which sets the contribution rate of other volume data in volume rendering of the volume data selected by the second volume selection section 220; and a second rendering operation section 222 which creates a second projected image by performing volume rendering of the selected volume data on the basis of the set contribution rate.

The projected image combination section 203 includes: a combination rate setting section 204 which sets the combination rate of each of the first and second projected images; a first multiplication section 206 which multiplies the first projected image by the combination rate set by the combination rate setting section 204; a second multiplication section 207 which multiplies the second projected image by the combination rate set by the combination rate setting section 204; and a combination section 208 which combines the first and second projected images multiplied by the combination rate and outputs the composite projected image to the combination processing unit 121.

In addition, as shown in FIG. 3, the display unit 122 displays: a first volume data selection frame 310 which corresponds to the first volume data selection section 210 and which is for selecting predetermined volume data from the plurality of types of volume data stored in the volume data storage unit 119; and a second volume data selection frame 312 which corresponds to the second volume data selection section 220 and which is for selecting predetermined volume data from the plurality of types of volume data stored in the volume data storage unit 119. In addition, the display unit 122 displays a selection mark 320 on the selected volume data so that the volume data selected by the first volume selection section 210 or the second volume data selection section 220 can be recognized. The operator can select predetermined volume data by setting the selection mark 320 for the plurality of types of volume data.

The display unit 122 displays: a first projected image contribution rate frame 314 which corresponds to the first contribution rate setting section 214 and which is for setting the contribution rate in volume rendering of the first projected image; and a second projected image contribution rate frame 316 which corresponds to the second contribution rate setting section 224 and which is for setting the contribution rate in volume rendering of the second projected image. The contribution rates set by the first and second contribution rate setting sections 214 and 224 are shown as the numeric values of {K1, K2, K3, K4, K5, K6}. The operator can set the contribution rate by setting the numeric value for each of the plurality of contribution rates. Details thereof will be described later.

In addition, the display unit 122 displays a combination rate display frame 318 which corresponds to the combination rate setting section 204 and which is for setting the combination rate of the first and second projected images using a combination rate setting bar 330. The operator can set the combination rate by operating the combination rate setting bar 330.

In the present embodiment, as indicated by the selection mark 320 in FIG. 3, for example, the first volume data selection section 210 selects tomographic volume data and blood flow volume data, and the second volume data selection section 220 selects tomographic volume data, blood flow volume data, and elastic volume data.

The first contribution rate setting section 214 sets the contribution rate of the output pixel value in volume rendering of the first rendering operation section 212. In addition, when performing volume rendering of certain volume data, the first rendering operation section 212 performs the volume rendering in consideration of information of other volume data and the set contribution rate. Specifically, the first rendering operation section 212 creates a first projected image by performing volume rendering according to the following Expression. The contribution rate set by the first contribution rate setting section 214 is displayed as {K1, K2, K3, K4, K5, K6}.

Expressions (1.1) to (1.3) are Expressions in volume rendering of tomographic volume data, Expressions (1.4) to (1.6) are Expressions in volume rendering of blood flow volume data, and Expressions (1.7) to (1.9) are Expressions in volume rendering of elastic volume data.

{Expression 1}

$$Cout(i)=Cout(i-1)+X(i)\cdot(1-Xout(i-1))\cdot C(i)\cdot S(i)\\(1-K1\cdot Yout(i-1))\cdot(1-K2\cdot Zout(i-1)) \quad (1.1)$$

$$Xout(i)=Xout(i-1)+(1-Xout(i-1))\cdot X(i) \quad (1.2)$$

$$X(i)=\text{Opacity}X[C(i)] \quad (1.3)$$

$$Dout(i)=Dout(i-1)+Y(i)\cdot(1-Yout(i-1))\cdot D(i)\cdot T(i)\cdot(1-\\K3\cdot Xout(i-1))\cdot(1-K4\cdot Zout(i-1)) \quad (1.4)$$

$$Yout(i) = Yout(i-1) + (1 - Yout(i-1)) \cdot Y(i) \quad (1.5)$$

$$Y(i) = OpacityY[D(i)] \quad (1.6)$$

$$Eout(i) = Eout(i-1) + Z(i) \cdot (1 - Zout(i-1)) \cdot E(i) \cdot U(i) \cdot (1 - K5 \cdot Xout(i-1)) \cdot (1 - K6 \cdot Yout(i-1)) \quad (1.7)$$

$$Zout(i) = Zout(i-1) + (1 - Zout(i-1)) \cdot Z(i) \quad (1.8)$$

$$Z(i) = OpacityZ[E(i)] \quad (1.9)$$

First, Expressions (1.1) to (1.3) will be described. $C(i)$ is an i-th brightness value existing on the line of sight when a three-dimensional tomographic image is viewed from a certain point on the created two-dimensional projection plane. $Cout(i)$ is an output pixel value. For example, when the brightness values of N voxels are aligned on the line of sight, the brightness value $Cout(N-1)$ obtained by integration from $i=0$ to $N-1$ is a pixel value which is eventually output. $Cout(i-1)$ indicates an integrated value up to the $(i-1)$-th value.

In addition, OpacityX is a tomographic opacity table which takes the values of 0 to 1.0. $X(i)$ is the opacity of the i-th brightness value existing on the line of sight. As shown in Expression (1.3), the opacity on the output two-dimensional projection plane (three-dimensional tomographic image) is determined by referring to the tomographic opacity table OpacityX from the brightness value.

$S(i)$ is a weight component for shading which is calculated from the brightness $C(i)$ and the gradient calculated from the surrounding pixel values. For example, $S(i)$ indicates the emphasis effect, such as "when a light source and the normal line of the plane having a voxel i at the center match each other, 1.0 is given since the strongest reflection occurs" and "when the light source and the normal line are perpendicular to each other, 0.0 is given".

In Expressions (1.1) and (1.2), both $Cout(i-1)$ and $Xout(i-1)$ in the case of $i=0$ are initialized to 0. As shown in Expression (1.2), $Xout(i)$ is integrated on each pass through a voxel to converge on 1.0. Accordingly, as shown in Expression (1.1), when the integrated value $Xout(i-1)$ of the opacity up to the $(i-1)$-th value has converged on 1.0, the brightness value $C(i)$ from the i-th value is not reflected on the output image.

In addition, Expression (1.1) includes $(1-K1 \cdot Yout(i-1))$ and $(1-K2 \cdot Zout(i-1))$ as coefficients. The pixel value $Cout(i)$ is calculated on the basis of the integrated value of the opacity up to the $(i-1)$-th value in volume rendering of not only the tomographic volume data but also the blood flow volume data and the elastic volume data.

Next, Expressions (1.4) to (1.6) will be described. $D(i)$ is an i-th blood flow value (for example, speed) existing on the line of sight when a three-dimensional blood flow image is viewed from a certain point on the created two-dimensional projection plane. $Dout(i)$ is an output pixel value. For example, when the blood flow values of N voxels are aligned on the line of sight, the blood flow value $Dout(N-1)$ obtained by integration from $i=0$ to $N-1$ is a pixel value which is eventually output. $Dout(i-1)$ indicates an integrated value up to the $(i-1)$-th value.

In addition, OpacityY is a blood flow opacity table which takes the values of 0 to 1.0. $Y(i)$ is the opacity of the i-th blood flow value existing on the line of sight. As shown in Expression (1.6), the opacity on the output two-dimensional projection plane (three-dimensional blood flow image) is determined by referring to the blood flow opacity table OpacityY from the blood flow value.

$T(i)$ is a weight component for shading which is calculated from the blood flow value $D(i)$ and the gradient calculated from the surrounding pixel values. For example, $T(i)$ indicates the emphasis effect, such as "when a light source and the normal line of the plane having a voxel i at the center match each other, 1.0 is given since the strongest reflection occurs" and "when the light source and the normal line are perpendicular to each other, 0.0 is given".

In Expressions (1.4) and (1.5), both $Dout(i-1)$ and $Yout(i-1)$ in the case of $i=0$ are initialized to 0. As shown in Expression (1.5), $Yout(i)$ is integrated on each pass through a voxel to converge on 1.0. Accordingly, as shown in Expression (1.4), when the integrated value $Yout(i-1)$ of the opacity up to the $(i-1)$-th value reaches appropriately 1.0, the blood flow value $D(i)$ from the i-th value is not reflected on the output image.

In addition, Expression (1.4) includes $(1-K3 \cdot Xout(i-1))$ and $(1-K4 \cdot Zout(i-1))$ as coefficients. The pixel value $Dout(i)$ is calculated on the basis of the integrated value of the opacity up to the $(i-1)$-th value in volume rendering of not only the blood flow volume data but also the tomographic volume data and the elastic volume data.

Next, Expressions (1.7) to (1.9) will be described. $E(i)$ is an i-th value of elasticity (for example, strain, elastic modulus, displacement, viscosity, or distortion ratio) existing on the line of sight when a three-dimensional elastic image is viewed from a certain point on the created two-dimensional projection plane. $Eout(i)$ is an output pixel value. For example, when the values of elasticity of N voxels are aligned on the line of sight, the value of elasticity $Eout(N-1)$ obtained by integration from $i=0$ to $N-1$ is a pixel value which is eventually output. $Eout(i-1)$ indicates an integrated value up to the $(i-1)$-th value.

In addition, OpacityZ is an elastic opacity table which takes the values of 0 to 1.0. $E(i)$ is the opacity of the i-th value of elasticity existing on the line of sight. As shown in Expression (1.9), the opacity on the output two-dimensional projection plane (three-dimensional elastic image) is determined by referring to the elastic opacity table OpacityZ from the value of elasticity.

$U(i)$ is a weight component for shading which is calculated from the value of elasticity $E(i)$ and the gradient calculated from the surrounding pixel values. For example, $U(i)$ indicates the emphasis effect, such as "when a light source and the normal line of the plane having a voxel i at the center match each other, 1.0 is given since the strongest reflection occurs" and "when the light source and the normal line are perpendicular to each other, 0.0 is given".

In Expressions (1.7) and (1.8), both $Eout(i-1)$ and $Zout(i-1)$ in the case of $i=0$ are initialized to 0. As shown in Expression (1.8), $Zout(i)$ is integrated on each pass through a voxel to converge on 1.0. Accordingly, as shown in Expression (1.7), when the integrated value $Zout(i-1)$ of the opacity up to the $(i-1)$-th value reaches approximately 1.0, the value of elasticity $E(i)$ from the i-th value is not reflected on the output image.

In addition, Expression (1.7) includes $(1-K5 \cdot Xout(i-1))$ and $(1-K6 \cdot Yout(i-1))$ as coefficients. The pixel value $Eout(i)$ is calculated on the basis of the integrated value of the opacity up to the $(i-1)$-th value in volume rendering of not only the elastic volume data but also the tomographic volume data and the blood flow volume data.

In the present embodiment, as shown in FIG. 3, the contribution rates {K1, K2, K3, K4, K5, K6} set by the first contribution rate setting section 214 are set to {1.0, 1.0, 1.0, 1.0, 1.0, 1.0}.

Similar to the first projected image creation section 200, the second contribution rate setting section 224 of the second projected image creation section 202 sets the contribution rate of the output in volume rendering of the second rendering operation section 222. In addition, when performing volume rendering of certain volume data, the second rendering operation section 222 creates a second projected image by performing volume rendering in consideration of the contribution rate based on the output image of other volume data. Specifically, since this is the same as Expressions (1.1) to (1.9) described above, the explanation will be omitted. In the present embodiment, as shown in FIG. 3, the contribution rates {K1, K2, K3, K4, K5, K6} set by the second contribution rate setting section 224 are set to {1.0, 0.0, 1.0, 0.0, 0.0, 0.0}.

The first and second projected image creation sections 200 and 202 create first and second projected images by rendering volume data to which a tomographic code, an elastic code, and a blood flow code are given, respectively. In the first and second projected image creation sections 200 and 202, images created by rendering volume data configured to include a tomographic code become tomographic images of the first and second projected images, images created by rendering volume data configured to include an elastic code become elastic images of the first and second projected images, and images created by rendering volume data configured to include a blood flow code become blood flow images of the first and second projected images.

In addition, the projected image combination section 203 creates a composite projected image using the following Expression.

{Expression 2}

Composite tomographic image=α×(tomographic image of first projected image)+β×(tomographic image of second projected image)

Composite elastic image=α×(elastic image of first projected image)+β×(elastic image of second projected image)

Composite blood flow image=α×(blood flow image of first projected image)+β×(blood flow image of second projected image)

α+β=1

The composite tomographic image is obtained by combining the tomographic codes in the tomographic images of the first and second projected images at the predetermined combination rate, the composite elastic image is obtained by combining the elastic codes in the elastic images of the first and second projected images at the predetermined combination rate, and the composite blood flow image is obtained by combining the blood flow codes in the blood flow images of the first and second projected images at the predetermined combination rate. The composite projected image is obtained by adding the composite tomographic image, the composite elastic image, and the composite blood flow image for respective coordinates of the two-dimensional projection plane.

The combination rate setting section 204 sets the combination rates α and β of the first and second projected images under the control of the control unit 103 based on the operation of the operating unit 104. The combination rates α and β are equal to or greater than 0 and equal to or less than 1. As shown in FIG. 3, the combination rate setting bar 330 for setting the combination rates of the first and second projected images is displayed on the combination rate display frame 318.

When the combination rate setting bar 330 is placed on the left side of the center, the combination rate setting section 204 increases the combination rate a so that the first projected image is emphasized over the second projected image. The combination rate setting section 204 may reduce the combination rate β.

When the combination rate setting bar 330 is placed on the right side of the center, the combination rate setting section 204 reduces the combination rate a so that the second projected image is emphasized over the first projected image. The combination rate setting section 204 may increase the combination rate β.

The first multiplication section 206 which multiplies the first projected image by the combination rate set by the combination rate setting section 204 and the second multiplication section 207 which multiplies the second projected image by the combination rate set by the combination rate setting section 204 are equivalent to the multiplication in the above Expression. In addition, the combination section 208 which combines the first and second projected images and outputs the composite projected image to the combination processing unit 121 is equivalent to the addition in the above Expression.

As shown in FIG. 3, the display unit 122 displays a composite projected image 300 created by the composite projected image creation unit 120 in a state set by selection of volume data and various parameters, such as the contribution rate and the combination rate. The operator can set various parameters while checking the composite projected image 300.

For example, when it is necessary to display blood flow information mainly on the composite projected image 300, the combination rate a of the first projected image configured to include tomographic volume data and blood flow volume data is increased. In addition, when it is necessary to display elastic information mainly on the composite projected image 300, the combination rate β of the second projected image configured to include tomographic volume data, blood flow volume data, and elastic volume data is increased. In addition, when the operator has set the combination rate α to 0.5, the composite projected image 300 can be created as an image in which both regions where tomographic information and elastic information overlap are mixed.

The combination processing unit 121 sets the RGB values for respective coordinates of the two-dimensional projection plane of the tomographic code obtained by converting the composite tomographic image created by the composite projected image creation unit 120, the blood flow code obtained by converting the composite blood flow image, and the elastic code obtained by converting the composite elastic image, and performs combination and coloring processing for each component of RGB on the basis of "composite projected image=composite tomographic image+composite elastic image+composite blood flow image". In addition, the combination processing unit 121 may also perform processing for combining the colored composite projected image with a two-dimensional tomographic image, a two-dimensional elastic image, or a two-dimensional blood flow image. The display unit 122 displays the colored composite projected image.

Accordingly, the composite projected image 300 can be made as a composite projected image in which tissue 302 that can be checked from the tomographic information, a tumor portion 304 having predetermined hardness from the elastic information, and a blood flow portion 306 surrounding the tumor portion 304 can be checked.

In addition, although the coloring processing is performed on the composite projected image by the combination processing unit 121 in the present embodiment, coloring may be performed in advance for the volume data stored in the volume data storage unit 119.

Shading information (RGB values of white and black) is given to each point of tomographic volume data stored in the volume data storage unit 119 according to the signal strength. In addition, color information (RGB values of blue, light blue, green, yellow, red, and the like) is given to each point of elastic volume data according to the value of elasticity. Color information (RGB values of blue, red, green, and the like) is given to each point of blood flow volume data according to the blood flow information (blood flow speed, blood flow direction, dispersion).

In addition, the first and second rendering operation sections 212 and 222 perform rendering using the following Expressions instead of Expressions (1.1) to (1.9). Here, differences from Expressions (1.1) to (1.9) will mainly be described.

{Expression 3}

$$Cout(i)=Cout(i-1)+X(i)\cdot(1-Xout(i1))\cdot C(i)\cdot S(i) \quad (3.1)$$

$$Xout(i)=Xout(i-1)+(1-Xout(i-1))\cdot\{X(i)+K1\cdot Y(i)+K2\cdot Z(i)\} \quad (3.2)$$

$$X(i)=OpacityX[C(i)] \quad (3.3)$$

$$Dout(i)=Dout(i-1)+Y(i)\cdot(1-Yout(i-1))\cdot D(i)\cdot T(i) \quad (3.4)$$

$$Yout(i)=Yout(i-1)+(1-Yout(i-1))\cdot\{K3\cdot X(i)+Y(i)+K4\cdot Z(i)\} \quad (3.5)$$

$$Y(i)=OpacityY[D(i)] \quad (3.6)$$

$$Eout(i)=Eout(i-1)+Z(i)\cdot(1-Zout(i-1))\cdot E(i)\cdot U(i) \quad (3.7)$$

$$Zout(i)=Zout(i-1)+(1-Zout(i-1))\cdot\{K5\cdot X(i)+K6\cdot Y(i)+Z(i)\} \quad (3.8)$$

$$Z(i)=OpacityZ[E(i)] \quad (3.9)$$

The first and second rendering operation sections 212 and 222 perform rendering of each component of RGB for respective coordinates of the two-dimensional projection plane using Expressions (3.1) to (3.9).

In order to create the first projected image R, the first rendering operation section 212 performs the operations of Expressions (3.1) to (3.9) using the contribution rate with the R component of the brightness of the tomographic image, the R component of the brightness of the blood flow image, and the R component of the brightness of the elastic image as C(i), D(i), and E(i), respectively, and adds these results to create the first projected image R.

Similarly, in order to create the first projected image G, the first rendering operation section 212 performs the operations of Expressions (3.1) to (3.9) with the G components of the tomographic image, the blood flow image, and the elastic image as C(i), D(i), and E(i), respectively, and adds these results. In addition, in order to create the first projected image B, the first rendering operation section 212 performs the operations of Expressions (3.1) to (3.9) with the B components of the respective images as C(i), D(i), and E(i), respectively, and adds these results.

Similarly, the second rendering operation section 222 creates the second projected image for the coordinates of the two-dimensional projection plane using the contribution rate.

In addition, as the opacity table used in Expressions (3.1) to (3.9), the first and second rendering operation sections 212 and 222 may use different opacity table.

Next, how the projected image combination section 203 combines the first and second projected images to create a composite projected image will be described. The projected image combination section 203 combines the RGB values of a plurality of projected images for respective coordinates of the two-dimensional projection plane using the following Expression and creates a composite projected image.

{Expression 4}

Composite projected image $R=\alpha\times$(first projected image $R$)$+\beta\times$(second projected image $R$)

Composite projected image $G=\alpha\times$(first projected image $G$)$+\beta\times$(second projected image $G$)

Composite projected image $B=\alpha\times$(first projected image $B$)$+\beta\times$(second projected image $B$)

$\alpha+\beta=1$

In addition, since the combination rate $\alpha$, the combination rate $\beta$, the combination rate setting bar 330, and the like are the same as in Expression 2 described above, explanation thereof will be omitted herein.

Figure 4:
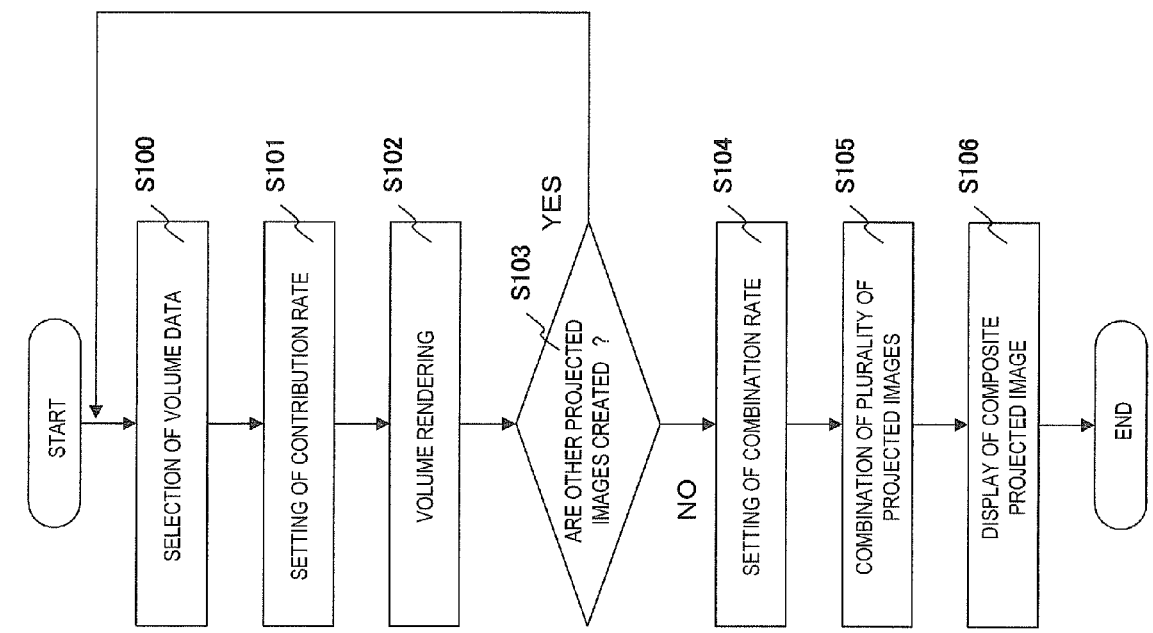
FIG. 4 is a flow chart showing the operation procedure of the present invention.
Figure 5:
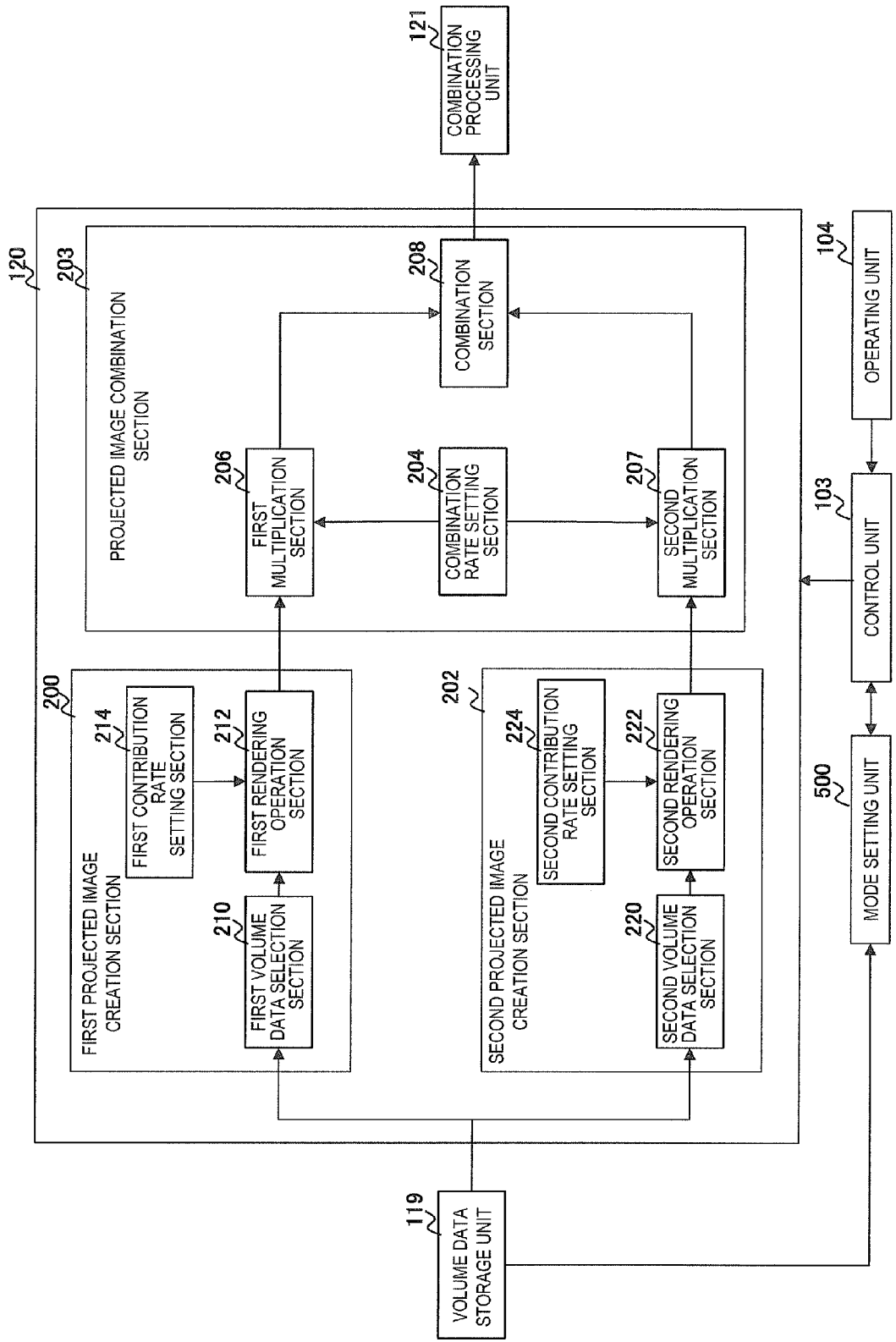
FIG. 5 is a view showing the details of a composite projected image creation unit 120 in second and third embodiments of the present invention.

Next, the operation procedure in the present embodiment will be described using FIG. 4.

(S100) The first volume selection section 210 or the second volume selection section 220 selects volume data, which is used for creation of a projected image, from the tomographic volume data, the elastic volume data, and the blood flow volume data stored in the volume data storage unit 119 under the control of the control unit 103 based on the operation of the operating unit 104.

(S101) The first contribution rate setting section 214 or the second contribution rate setting section 224 sets the contribution rate in volume rendering of the selected volume data under the control of the control unit 103 based on the operation of the operating unit 104.

(S102) Under the control of the control unit 103 based on the operation of the operating unit 104, it is selected whether to create another projected image to be combined. When creating another projected image to be combined, the process returns to S100 to create a projected image again. Although two projected images to be combined were created in the present embodiment, three or more projected images may be created.

(S103) The combination rate setting section 204 sets the combination rate of the first and second projected images, which are to be combined with each other, under the control of the control unit 103 based on the operation of the operating unit 104.

(S104) The combination section 208 creates a composite projected image by combining the first and second projected images, which are to be combined with each other, on the basis of the set combination rate.

(S105) The display unit 122 displays the composite projected image.

As described above, according to the present embodiment, it is possible to display the three-dimensional elastic image, the three-dimensional blood flow image, and the three-dimensional tomographic image such that each of the images can be recognized as a composite projected image. That is, the operator can check the positional relationship of tomographic information enabling tissue to be checked, elastic information enabling the hardness information to be checked, and a blood flow image enabling the blood flow information to be checked in a three-dimensional manner in the composite projected image.

In addition, it is also possible to read any one of the tomographic volume data, the elastic volume data, and the blood flow volume data from the volume data storage unit 119 and to combine projected images created from the respective volume data items. Specifically, the first projected image creation section 200 creates a first projected image by performing volume rendering of any one volume data (for example, tomographic volume data) among the tomographic volume data, the elastic volume data, and the blood flow volume data stored in the volume data storage unit 119. In addition, the second projected image creation section 202 creates a second projected image by performing volume rendering of any one volume data (for example, elastic volume data) among the tomographic volume data, the elastic volume data, and the blood flow volume data stored in the volume data storage unit 119. The projected image combination section 203 combines the first and second projected images on the basis of the predetermined contribution rate as described above.

In addition, although the volume rendering has been specifically described in the present embodiment, other rendering techniques, such as surface rendering, may also be adopted in addition to the volume rendering.

Next, a second embodiment will be described using FIGS. 1 to 6. The second embodiment is different from the first embodiment in that the combination rate of the first and second projected images can be set automatically.

In order to set a preferred display mode for preferred display in a composite projected image, a mode setting unit 500 that sets a tomographic mode, a blood flow mode, and an elastic mode is provided. The mode setting unit 500 is connected to the control unit 103. In addition, as shown in FIG. 6, the display unit 122 displays a mode setting frame 600 which corresponds to the mode setting unit 500 and which is for setting a preferred display mode. A mode setting mark 602 is given to the set preferred display mode. On the basis of the preferred display mode set by the mode setting unit 500, the control unit 103 controls each component of the composite projected image creation unit 120. On the basis of the preferred display mode set by the mode setting unit 500, the combination rate setting section 204 mainly sets the combination rate of the first and second projected images.

In the present embodiment, as indicated by the mode setting mark 602 in FIG. 6, an elastic mode (preferred display mode) is set. Either of the first volume data selection section 210 in the first projected image creation section 200 and the second volume data selection section 220 in the second projected image creation section 202 selects the volume data such that the elastic volume data is included. The first and second rendering operation sections 212 and 222 perform volume rendering as described in the first embodiment. It is assumed that the elastic volume data is included in the first projected image.

On the basis of the set elastic mode, the combination rate setting section 204 sets the combination rate such that the combination rate of the first projected image obtained by performing volume rendering using volume data with elastic volume data is higher than the combination rate of the other second projected image. Specifically, the combination rate setting section 204 sets the combination rate of the first projected image obtained by performing volume rendering using volume data with elastic volume data to be higher than 0.5. In addition, the combination section 208 combines the first and second projected images at the set combination rate to create a composite projected image.

Therefore, since the combination rate of the first projected image having the elastic volume data is higher than the combination rate of the other second projected image, elastic information in the composite projected image is displayed without being hidden by other tissue. Accordingly, the operator can check all of three-dimensional elastic image and other images.

In addition, the display unit 122 displays a full auto setting frame 610 which corresponds to the mode setting unit 500 and which is for setting a full auto mode. When the full auto mode is set, the display unit 122 gives a check mark 612. On the basis of the full auto mode set by the mode setting unit 500, the control unit 103 controls each component of the composite projected image creation unit 120.

Specifically, the mode setting unit 500 is provided at the output side of the volume data storage unit 119. The mode setting unit 500 analyzes each item of the volume data and sets various parameters. First, the mode setting unit 500 calculates whether the value of elasticity of elastic volume data exceeds a predetermined threshold value. The value of elasticity of elastic volume data is an average value, a median, or the like. The average value of elastic volume data is a value obtained by adding all values of elasticity of elastic volume data and dividing the result by the total number of elastic volume data. The median of elastic volume data is a value located in the middle of the hardest value of elasticity and the softest value of elasticity in the values of elasticity of elastic volume data.

Moreover, when the value of elasticity of elastic volume data does not exceed the threshold value, the mode setting unit 500 sets the combination rate such that the combination rate of the first projected image obtained by performing volume rendering using volume data with elastic volume data is higher than the combination rate of the other second projected image. When the value of elasticity of elastic volume data exceeds the threshold value, the mode setting unit 500 sets the combination rate such that the combination rate of the first projected image obtained by performing volume rendering using volume data with elastic volume data is lower than the combination rate of the other second projected image.

In addition, although the combination rate of the first and second projected images is set using the value of elasticity of elastic volume data in the present embodiment, it is also possible to set the combination rate of the first and second projected images using the blood flow value of blood flow volume data.

As described above, according to the present embodiment, it is possible to appropriately display the three-dimensional elastic image, the three-dimensional blood flow image, and the three-dimensional tomographic image such that each of the images can be recognized as a composite projected image. Accordingly, the operator can check all of three-dimensional elastic image, three-dimensional blood flow image, and three-dimensional tomographic image.

Next, a third embodiment will be described using FIGS. 1 to 6. The third embodiment is different from the first and second embodiments in that the contribution rates of the first and second projected images can be set automatically.

On the basis of the preferred display mode set by the mode setting unit 500 shown in the second embodiment, the first contribution rate setting section 214 or the second contribution rate setting section 224 sets the contribution rate. In the present embodiment, as indicated by the mode setting mark 602 in FIG. 6, an elastic mode (preferred display mode) is set. The first contribution rate setting section 214 or the second contribution rate setting section 224 sets the contribution rate on the basis of the set elastic mode. Specifically, the first contribution rate setting section 214 or the second contribution rate setting section 224 sets the contribution rates {K1, K2, K3, K4, K5, K6} related to the elastic volume data to {0.0, 1.0, 0.0, 1.0, 0.0, 0.0}.

Specifically, the first contribution rate setting section 214 or the second contribution rate setting section 224 reduces the contribution rate of other volume rendering related to the volume rendering of elastic volume data (for example, sets K5 and K6 to 0) or increases the contribution rate of volume rendering of elastic volume data related to the volume rendering of other volume data (for example, sets K2 and K4 to 1), so that priority is given to the volume rendering of the elastic volume data. By performing volume rendering of the elastic elastic volume data in this manner in order to combine the first and second projected images, elastic information in the composite projected image is displayed without being hidden by other tissue. Accordingly, the operator can check all of three-dimensional elastic image, three-dimensional blood flow image, and three-dimensional tomographic image.

REFERENCE SIGNS LIST

- 100: ultrasonic diagnostic apparatus
- 102: ultrasonic probe
- 103: control unit
- 104: operating unit
- 105: signal transmission unit
- 106: signal receiving unit
- 107: signal transmission and reception control unit
- 108: phasing addition unit
- 109: data storage unit
- 113: two-dimensional tomographic image creation unit
- 114: tomographic volume data generation unit
- 115: two-dimensional elastic image creation unit
- 116: elastic volume data generation unit
- 117: two-dimensional blood flow image creation unit
- 118: blood flow volume data generation unit
- 119: volume data storage unit
- 120: composite projected image creation unit
- 121: combination processing unit
- 122: display unit

The invention claimed is:

1. An ultrasonic diagnostic apparatus comprising:
   an ultrasonic probe having transducers through which an ultrasonic wave is transmitted and received;
   a signal transmission unit that transmits an ultrasonic wave to an object through the ultrasonic probe;
   a signal receiving unit that receives a reflected echo signal reflected from the object;
   a display unit that creates a projected image by rendering volume data based on the reflected echo signal and displays the projected image;
   a first volume data generation unit that generates a first type of volume data based on at least one first image;
   a second volume data generation unit that generates a second type of volume data based on at least one second image;
   a third volume data generation unit that generates a third type of volume data based on at least one third image;
   a first projected image creation unit which creates a first projected image using volume data selected from at least some of the first, second and third types of volume data,
   wherein the first projected image creation unit includes a first volume selection section which selects predetermined volume data from the at least some of the first, second and third types of volume data, a first contribution rate setting section which sets a contribution rate of other volume data in rendering of the volume data selected by the first volume selection section, and a first rendering operation section which creates the first projected image by rendering the selected volume data on the basis of the set contribution rate;
   a second projected image creation unit, which creates a second projected image different from the first projected image using volume data selected from at least some of the first, second and third types of volume data,
   the second projected image creation section includes a second volume selection section which selects predetermined volume data from the at least some of the first, second and third types of volume data, a second contribution rate setting section which sets a contribution rate of other volume data in rendering of the volume data selected by the second volume selection section, and a second rendering operation section which creates a second projected image by rendering the selected volume data on the basis of the set contribution rate; and
   a projected image combination unit that creates a composite projected image by combining the first and second projected images on the basis of a predetermined combination rate of the first and second projected images, and
   the display unit displays the composite projected image.

2. The ultrasonic diagnostic apparatus according to claim 1,
   wherein the display unit displays a combination rate display frame for setting the combination rate of the first and second projected images.

3. The ultrasonic diagnostic apparatus according to claim 2,
   wherein a combination rate setting bar for setting the combination rate of the first and second projected images is displayed on the combination rate display frame.

4. The ultrasonic diagnostic apparatus according to claim 1,
   wherein the first, second and third types of volume data are tomographic volume data, elastic volume data, and blood flow volume data calculated on the basis of the reflected echo signal.

5. The ultrasonic diagnostic apparatus according to claim 1,
   wherein the projected image combination unit includes:
   a combination rate setting section which sets a combination rate of each of the first and second projected images;
   a first multiplication section which multiplies the first projected image by the combination rate set by the combination rate setting section;
   a second multiplication section which multiplies the second projected image by the combination rate set by the combination rate setting section; and
   a combination section which combines the first and second projected images and outputs a composite projected image.

6. The ultrasonic diagnostic apparatus according to claim 5, further comprising:
   a mode setting unit that sets a preferred display mode for preferred display in the composite projected image,
   wherein the combination rate setting section sets the combination rate of the first and second projected images on the basis of the preferred display mode set by the mode setting unit.

7. The ultrasonic diagnostic apparatus according to claim 1, further comprising:
   a volume data storage unit that stores the first, second and third types of volume data.

8. The ultrasonic diagnostic apparatus according to claim 7, wherein the display unit displays a volume data selection frame for selecting predetermined volume data from the plurality of types of volume data.

9. The ultrasonic diagnostic apparatus according to claim 1,
wherein the first projected image creation unit creates the first projected image by performing volume rendering of any one volume data among tomographic volume data, elastic volume data, and blood flow volume data stored in a volume data storage unit, and
the second projected image creation unit creates the second projected image by performing volume rendering of any one volume data among tomographic volume data, elastic volume data, and blood flow volume data stored in the volume data storage unit.

10. The ultrasonic diagnostic apparatus according to claim 1,
wherein the display unit displays a first projected image contribution rate frame for setting the contribution rate in rendering of the first projected image and a second projected image contribution rate frame for setting the contribution rate in rendering of the second projected image.

11. The ultrasonic diagnostic apparatus according to claim 1, further comprising:
a mode setting unit that sets a preferred display mode for preferred display in the composite projected image,
wherein the first contribution rate setting section or the second contribution rate setting section sets each contribution rate on the basis of the preferred display mode set by the mode setting unit.

12. The ultrasonic diagnostic apparatus according to claim 1, wherein the first, second and third images are a tomographic image, an elastic image, and a blood flow image.

13. An ultrasonic image display method comprising:
generating first volume data based on at least one first image;
generating second volume data based on at least one second image;
generating third volume data based on at least one third image;
creating projected images from at least some of the first, second and third volume data based on a reflected echo signal of an ultrasonic wave,
wherein the creating the projected images included:
creating a first projected image using volume data selected from the plurality of types of volume data which includes:
selecting predetermined volume data from the plurality of types of volumes data,
setting a contribution rate of other volume data in rendering of the selected volume data, and
creating the first projected image by rendering the selected volume data on the basis of the set contribution rate; and
creating a second projected image different from the first projected image using volume data selected from the plurality of types of volume data which includes:
selecting predetermined volume data from the plurality of types of volume data,
setting a contribution rate of other volume data in rendering of the selected volume data, and
creating a second projected image by rendering the selected volume data on the basis of the set contribution rate;
creating a composite projected image by combining the plurality of projected images on the basis of a predetermined combination rate; and
displaying the composite projected image.

* * * * *